US012599100B2

(12) United States Patent
Nicolas et al.

(10) Patent No.: US 12,599,100 B2
(45) Date of Patent: Apr. 14, 2026

(54) PEPPER CULTIVAR NAVELITO

(71) Applicant: Syngenta Crop Protection AG, Basel (CH)

(72) Inventors: Matthieu Nicolas, Sarrians (FR); Benny Nir, Shikmim (IL)

(73) Assignee: SYNGENTA CROP PROTECTION AG, Basel (CH)

( * ) Notice: Subject to any disclaimer, the term of this patent is extended or adjusted under 35 U.S.C. 154(b) by 169 days.

(21) Appl. No.: 18/472,698

(22) Filed: Sep. 22, 2023

(65) Prior Publication Data

US 2025/0098623 A1 Mar. 27, 2025

(51) Int. Cl.
| | |
|---|---|
| *A01H 5/10* | (2018.01) |
| *A01H 5/08* | (2018.01) |
| *A01H 6/82* | (2018.01) |
| *C12Q 1/6895* | (2018.01) |

(52) U.S. Cl.
CPC .............. *A01H 6/822* (2018.05); *A01H 5/08* (2013.01); *C12Q 1/6895* (2013.01); *C12Q 2600/13* (2013.01); *C12Q 2600/156* (2013.01)

(58) Field of Classification Search
CPC .................................. A01H 5/10; A01H 6/822
See application file for complete search history.

(56) References Cited

U.S. PATENT DOCUMENTS

| | | |
|---|---|---|
| 8,957,286 B2 | 2/2015 | Shirai |
| 11,388,870 B2 * | 7/2022 | Noguera Diaz ......... A01H 5/08 |
| 2016/0165783 P1 | 6/2016 | Nir |

FOREIGN PATENT DOCUMENTS

WO 2008/152134 A1 12/2008

OTHER PUBLICATIONS

Haun et al., 2011, The Composition and Origins of Genomic Variation among Individuals of the Soybean Reference Cultivar Williams 82, Plant Physiology 155: 645-655. (Year: 2011).*
Großkinsky et al., 2015, Plant phenomics and the need for physiological phenotyping across scales to narrow the genotype-to-phenotype knowledge gap, Journal of Experimental Botany 66(18): 5429-5440. (Year: 2015).*
Applying for a Plant Variety Certificate of Protection by the USDA reference to Exhibit A; accessed May 1, 2023. (Year: 2023).*
UPOV EDV Explanatory Notes 14 and 30; Apr. 6, 2017. (Year: 2017).*

* cited by examiner

*Primary Examiner* — Bratislav Stankovic

(74) *Attorney, Agent, or Firm* — Karen A. Magri

(57) ABSTRACT

The present invention provides novel pepper plants and plant parts, seed, fruit, and tissue culture therefrom. The invention also provides methods for producing a pepper plant by crossing the pepper plants of the invention with themselves or another pepper plant. The invention also provides plants produced from such a crossing as well as plant parts, seed, fruit, and tissue culture therefrom.

21 Claims, No Drawings

PEPPER CULTIVAR NAVELITO

FIELD OF THE INVENTION

This invention is in the field of pepper plants.

BACKGROUND OF THE INVENTION

Peppers are a member of the night shade family, Solanaceae, and genus *Capsicum*. They are cultivated worldwide and used as a staple in many cuisines. *Capsicum* consists of five major species, *C. annuum, C. baccatum, C. chinense, C. frutescens*, and *C. pubescens* and is commonly broken into three groups: bell peppers, sweet peppers, and hot peppers. Additionally, they are used as a source to produce dried powders (e.g. paprika). Cultivated peppers can be distinguished by their pungency, fruit shape, color, and size. Peppers can be large, blocky, thin or thick-fleshed, long, blunt-ended, heart-shaped, elongate, or slender, among other characteristics (see for example U.S. Pat. No. 6,498,287).

Peppers represent an important and valuable crop. Thus, there is an ongoing need for improved pepper varieties having enhanced agronomic and/or consumer traits.

SUMMARY OF THE INVENTION

According to the invention, there is provided a novel hybrid pepper cultivar designated Navelito. Pepper cultivar Navelito is cytoplasmic male sterile (CMS) and parthenocarpic, producing seedless fruits that are orange at maturity. A CMS plant cannot produce viable pollen, act as a pollen donor (i.e., as a male parent) or self-pollinate, unless an appropriate restorer gene(s) is provided to restore male fertility. Because Navelito is male sterile (and does not comprise the restorer) and has a parthenocarpic trait, it can reliably produce seedless fruits by conventional cultivation methods, as long as fertilization by a male-fertile plant is avoided. In the presence of a male-fertile plant, pepper cultivar Navelito can be used in breeding as a female parent (i.e., pollen recipient), where the male-fertile parent plant can optionally be parthenocarpic or non-parthenocarpic and, further, can optionally comprise a restorer gene. Pepper cultivar Navelito is further characterized by its disease resistances (e.g., as shown in Table 1), including resistance against Tobamovirus pathotype 0 and Tomato Spotted Wilt Virus pathotype 0).

The invention also encompasses the seeds of pepper cultivar Navelito, the plants of pepper cultivar Navelito, parts of pepper cultivar Navelito (including fruit, seed, ovules, scion, rootstock, shoots), methods of producing seed from pepper cultivar Navelito, and methods for producing a pepper plant by crossing a pepper plant of cultivar Navelito (e.g., as female) with another pepper plant (e.g., as male), methods for producing a pepper plant comprising in its genetic material one or more transgenes, and the transgenic pepper plants produced by that method. The invention also relates to methods for producing other pepper plants derived from pepper cultivar Navelito, and pepper plants derived by the use of those methods. In embodiments, the plants and parts thereof of the invention are diploid plants and plant parts.

In embodiments, the pepper plants or parts thereof (e.g., fruit) of the invention are *Capsicum annuum* pepper plants or parts thereof. In embodiments, the pepper plants or parts thereof (e.g., fruit) of the invention are sweet *Capsicum*

*annuum* pepper plants or parts thereof, optionally producing a sweet or mild seedless fruit (i.e., in the absence of a male-fertile plant).

In another aspect, the present invention provides regenerable cells for use in tissue culture of pepper cultivar Navelito. In representative embodiments, the tissue culture is capable of regenerating plants having essentially all of the physiological and morphological characteristics of the foregoing pepper plant. In embodiments, the regenerate plants have substantially the same genotype as the foregoing pepper cultivar. Non-limiting examples of regenerable cells in such tissue cultures include meristematic cells, cotyledons, hypocotyl, leaves, embryos, roots, root tips, anthers, pistils, ovules, shoots, stems, petioles, pith, flowers, capsules, rootstock, scion and/or seeds as well as callus and/or protoplasts derived from any of the foregoing. Still further, the present invention provides plants regenerated from the tissue culture of the invention.

As a further aspect, the invention provides a method of producing pepper seed, the method comprising crossing a plant of pepper cultivar Navelito as female with a second pepper plant as male (i.e., pollen donor), optionally by hand-pollination. The second pepper plant acting as the male parent can optionally be parthenocarpic or non-parthenocarpic. Optionally, the method further comprises collecting the seed.

The invention further provides a method of producing a progeny pepper plant, the method comprising crossing a plant of pepper cultivar Navelito as female with a second pepper plant as male to produce at least a first progeny plant, optionally by hand pollination. The second pepper plant acting as the pollen donor can optionally be parthenocarpic or non-parthenocarpic.

As used herein, when a pepper plant is used in a cross "as male" (and similar terms), it is meant that the pepper plant is used as a pollen donor, i.e., produces fertile pollen. Unless indicated otherwise, the male parent can optionally comprise a parthenocarpic trait or alternatively does not comprise a parthenocarpic trait. Further, in embodiments, the male parent does not comprise a restorer of CMS.

In embodiments, a pepper plant or population of pepper plants derived from pepper cultivar Navelito comprises, on average, at least about 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from pepper cultivar Navelito, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pepper cultivar Navelito, and optionally may be the result of a breeding process comprising one or two breeding crosses and one or more of selfing, backcrossing and/or double haploid techniques in any combination and any order. In embodiments, the breeding process does not include a breeding cross, and comprises double haploid technology. In embodiments, the pepper plant derived from pepper cultivar Navelito is one, two, three, four, five or more breeding crosses removed from pepper cultivar Navelito.

In embodiments, a derived plant from pepper cultivar Navelito comprises a desired added trait(s). In representative embodiments, a pepper plant derived from pepper cultivar Navelito comprises some or all of the morphological and physiological characteristics of pepper cultivar Navelito (e.g., as described in Table 1). In embodiments, the pepper plant derived from pepper cultivar Navelito comprises essentially all of the morphological and physiological characteristics of pepper cultivar Navelito, (e.g., as described in Table 1), with the addition of a desired added trait(s).

The invention also relates to methods for producing a pepper plant comprising in its genetic material one or more transgenes and to the transgenic pepper plant produced by those methods. Also provided are plant parts, seed, fruit and tissue culture from such transgenic pepper plants, optionally wherein one or more cells in the plant part, seed, fruit or tissue culture comprise the transgene. The transgene can be introduced via plant transformation and/or breeding techniques.

In another aspect, the present invention provides for single locus converted plants of pepper cultivar Navelito. Plant parts, fruit and tissue culture from such single locus converted plants and seed producing such plants are also contemplated by the present invention. The single transferred locus may be a dominant or recessive allele. In illustrative embodiments, the single transferred locus will confer such traits as male fertility, herbicide resistance, pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, improved appearance (e.g., fruit color), industrial usage or any combination thereof. The single locus may be a naturally occurring pepper locus, a genome edited locus, a mutated locus (e.g., chemically or radiation induced), or a transgene introduced into pepper through genetic engineering techniques of the plant or a progenitor thereof (e.g., a parent line).

The invention further provides methods for developing pepper plants in a pepper plant breeding program using plant breeding techniques including without limitation recurrent selection, backcrossing, pedigree breeding, mutation breeding, double haploid techniques, restriction fragment length polymorphism enhanced selection, genetic marker enhanced selection, and/or transformation. Seeds, pepper plants, and parts thereof (including fruit), produced by such breeding methods are also part of the invention.

The invention also provides methods of multiplication or propagation of pepper plants of the invention, for example, via vegetative propagation.

The invention further provides a method of producing food or feed comprising (a) obtaining a pepper plant of the invention, wherein the plant has been cultivated to maturity, and (b) collecting a pepper fruit (e.g., a seedless pepper fruit) from the plant.

Additional aspects of the invention include harvested products and processed products from the pepper plants of the invention. A harvested product can be a whole plant or any plant part, as described herein. Thus, in some embodiments, a non-limiting example of a harvested product includes a seed, a fruit (immature or mature) or a part thereof, a rootstock, a scion, a shoot, a leaf, a stem, and the like.

In representative embodiments, a processed product includes, but is not limited to, cut, sliced, ground, pureed, dried, canned, jarred, packaged, frozen and/or heated fruit and/or seeds of the pepper plants of the invention, or any other part thereof. In embodiments, a processed product includes a flour, meal, sauce, salad, or puree containing a plant of the invention, or a part thereof (e.g., immature or mature fruit). In embodiments, the processed product includes washed and sliced fruit (immature or mature) or parts thereof of the invention.

Thus, the invention also provides a method of producing a processed product from a plant of the invention, the method comprising (a) obtaining a fruit of a plant of the invention; and (b) processing the fruit to produce a processed product. In embodiments, processing comprises slicing, cutting, dicing, dehydrating, pureeing, blanching and/or freezing.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed that produces a plant of pepper cultivar Navelito.

As a further aspect, the invention provides a plant of pepper cultivar Navelito.

As an additional aspect, the invention provides a pepper plant, or a part thereof, having all the physiological and morphological characteristics of a plant of pepper cultivar Navelito.

As another aspect, the invention provides fruit and/or seed of the pepper plants of the invention and a processed product from the fruit (e.g., immature or mature) and/or seed of the inventive pepper plants.

"Fruits" of the pepper plants of the invention can be seeded or seedless. In the case of a CMS and parthenocarpic pepper plant of the invention (e.g., pepper cultivar Navelito), the fruit will be seedless in the absence of a male-fertile parent and will be seeded in the presence of a male-fertile parent to provide fertile pollen.

As still another aspect, the invention provides a method of producing pepper seed, the method comprising crossing a pepper plant of the invention (optionally, as female) with a second pepper plant (optionally, as male). In embodiments, the cross is made by hand pollination. The second pepper plant acting as the male parent can optionally be parthenocarpic or non-parthenocarpic. The invention also provides seed produced by this method and plants produced by growing the seed.

The invention also provides as another aspect, a method of producing a pepper fruit (e.g., a seedless pepper fruit, the method comprising, growing a plant of pepper cultivar Navelito to produce a pepper fruit and, optionally, harvesting the pepper fruit from the plant. In embodiments, the method further comprises the step of planting the seed of pepper cultivar Navelito. Those skilled in the art will appreciate that the method is generally practiced in the absence of pollen from a male-fertile pepper plant.

As yet a further aspect, the invention provides a method for producing a seed of a pepper plant derived from pepper cultivar Navelito, the method comprising: (a) crossing a pepper plant of pepper cultivar Navelito as a female with a second pepper plant as a male (optionally, by hand pollination); and (b) allowing seed of a pepper plant derived from pepper Navelito to form. In embodiments, the method further comprises: (c) growing a plant from the seed of step (b) to produce a plant derived from pepper cultivar Navelito; (d) selfing the plant of step (c) or crossing it to a second pepper plant to form additional pepper seed derived from pepper cultivar Navelito; and (e) optionally repeating steps (c) and (d) one or more times (e.g., one, two, one to three, one to five, one to six, one to seven, one to ten, three to five, three to six, three to seven, three to eight or three to ten times) to generate further derived pepper seed from pepper cultivar Navelito, wherein in step (c) a plant is grown from the additional pepper seed of step (d) in place of growing a plant from the seed of step (b). In embodiments, the method comprises (e) repeating steps (c) and (d) one or more times (e.g., one to three, one to five, one to six, one to seven, one to ten, three to five, three to six, three to seven, three to eight or three to ten times) to generate further derived pepper seed. As another option, in embodiments, the method comprises collecting the pepper seed. The invention also provides seed produced by these methods and plants derived from pepper cultivar Navelito produced by growing the seed.

As another aspect, the invention provides a method of producing pepper fruit, the method comprising: (a) growing pepper cultivar Navelito; and (b) collecting fruit (e.g., seedless pepper fruit) from the plant. The invention also provides the fruit produced by this method.

Still further, as another aspect, the invention provides a method of vegetatively propagating a plant of pepper cultivar Navelito, the method comprising: (a) collecting tissue capable of being propagated from a plant of pepper cultivar Navelito; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

In representative embodiments, the invention also provides a method of producing a plant of pepper cultivar Navelito comprising a desired added trait, the method comprising introducing a transgene conferring the desired added trait into a plant of pepper Navelito (e.g., by transforming a progenitor of pepper cultivar Navelito, such as a parent line). The transgene can be introduced by transformation methods (e.g., genetic engineering) or breeding techniques. Plants produced by the method and progeny thereof are also provided. In embodiments, a plant comprising the transgene comprises the desired added trait and otherwise all the morphological and physiological characteristics of pepper cultivar Navelito.

The invention also provides pepper plants produced by the methods of the invention, wherein the pepper plant has the desired added trait as well as seed from such pepper plants.

According to the foregoing methods, the desired added trait can be any suitable trait known in the art including, for example, male fertility, herbicide resistance, pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, improved appearance (e.g., fruit color) industrial usage, or any combination thereof).

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode) encodes a *Bacillus thuringiensis* endotoxin.

In representative embodiments, plants of the invention, including without limitation, transgenic plants, single locus converted plants, and pepper plants derived from pepper cultivar Navelito are characterized by comprising both CMS and a parthenocarpic trait resulting in the production of seedless fruits (in the absence of a male fertile parent) that optionally are orange at maturity, and as a further option are triangular in shape. In embodiments, the plant further comprises one or more of the disease resistances of pepper cultivar Navelito (e.g., as shown in Table 1). In representative embodiments, plants of the invention, including without limitation, transgenic plants, single locus converted plants, and pepper plants derived from pepper cultivar Navelito, have at least 2, 3, 4, 5, 6, 7, 8, 9, 10 or more of the morphological and physiological characteristics of pepper cultivar Navelito (e.g., as described in Table 1), or even of all the morphological and physiological characteristics of pepper cultivar Navelito, so that said plants are not significantly different for said traits than pepper cultivar Navelito, as determined at the 5% significance level when grown in the same environmental conditions; optionally, with the presence of one or more desired additional traits (e.g., male fertility, disease resistance, pest or insect resistance, herbicide resistance, and the like).

The invention also encompasses plant parts, plant material, ovules, fruit and seed from the pepper plants of the invention. The invention also provides seeds that produce the pepper plants of the invention. Also provided is a tissue culture of regenerable cells from the pepper plants of the invention, where optionally, the regenerable cells are: (a) embryos, meristem, leaves, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are pepper plants regenerated from a tissue culture of the invention.

In still yet another aspect, the invention provides a method of determining a genetic characteristic of pepper cultivar Navelito or a progeny thereof using molecular genetic techniques, e.g., a method of determining a genotype of pepper cultivar Navelito or a progeny thereof. In embodiments, the method comprises detecting in the genome of a Navelito plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

These and other aspects of the present invention are set forth in the detailed description of the invention below.

DETAILED DESCRIPTION OF THE INVENTION

The present invention is based, in part, on the development of a novel pepper cultivar Navelito having desirable characteristics such as the production of orange seedless fruits at maturity. Navelito is CMS and comprises a parthenocarpic trait, resulting in reliable production of seedless fruits.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

All publications, patent applications, patents, and other references mentioned herein are incorporated by reference in their entirety.

I. Definitions

In the description and tables which follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, *In re Herz,* 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first-generation hybrid $F_1$ with one of the parental genotypes of the $F_1$ hybrid.

"Cotyledon". One of the first leaves of the embryo of a seed plant; typically, one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1n chromosomes. The chromosomes in these plantlets are then induced to "double" (e.g., using chemical means) resulting in cells containing 2n chromosomes. The progeny of these plantlets is termed "double haploid" and are essentially non-segregating (e.g., are stable). The term "double haploid" is used interchangeably herein with "dihaploid."

"Essentially all the physiological and morphological characteristics". A plant having "essentially all the physiological and morphological characteristics" (and similar phrases) means a plant having all of the desired physiological and morphological characteristics of the reference plant (e.g., as a recurrent parent), except for the characteristic(s) derived from the converted locus/loci (e.g., a single converted locus), for example, introduced via backcrossing to a progenitor of a pepper cultivar of the invention (e.g., a parent line), a modified gene(s) resulting from genome editing techniques, an introduced transgene (i.e., introduced via genetic transformation techniques or mutation (e.g., chemical or radiation induced), when both plants are grown under the same environmental conditions. In embodiments, a pepper plant having "essentially all of the physiological and morphological characteristics" of Navelito is CMS and parthenocarpic and produces seedless fruits that are optionally orange at maturity (e.g., in the absence of a male-fertile pepper plant) and as a further option are triangular in shape. The pepper plant may optionally further be characterized by comprising one or more of the disease resistances of pepper cultivar Navelito (e.g., as shown in Table 1). In embodiments, a plant having "essentially all of the physiological and morphological characteristics" means a plant having all of the characteristics of the reference plant with the exception of five or fewer traits, four or fewer traits, three or fewer traits, two or fewer traits, or one trait. In embodiments, a plant having "essentially all of the physiological and morphological characteristics" of pepper Navelito comprises the traits of Table 1.

"Gene". As used herein, "gene" refers to a segment of nucleic acid comprising an open reading frame. A gene can be introduced into a genome of a species, whether from a different species or from the same species, using transformation or various breeding methods.

The expression "immature harvestable stage" is understood herein to refer to a stage in the pepper fruit development where the fruit, having reached essentially full physiological development (e.g., cell division and expansion being essentially complete, fruit size and pericarp thickness having reached essentially maximum values), has not yet gone through the ripening process, e.g., are still an immature green color.

"Inbred line". As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Parthenocarpy". As used herein, "parthenocarpy" refers to the ability of a plant to produce fruits without fertilization of the ovules. Typically, fruits generated through partheno-carpy are seedless. Parthenocarpy can be genetically deter-mined or in some cases determined by manipulating the cultivation environment (e.g., temperature and daylight hours). Pepper cultivar Navelito comprises a genetically determined parthenocarpic trait, resulting in reliable produc-tion of seedless fruits (in the absence of a male-fertile pepper plant).

"Pepper". As used herein, the term "pepper" or "pepper plant" includes any plant classified as a *Capsicum*, including *C. annuum, C. baccatum, C. chinense, C. frutescens* and *C. pubescens*. Pepper plants include varieties, cultivars and populations of *Capsicum*. In embodiments, the pepper (or part thereof, such as fruit or seed) is a *C. annuum*. Further, the pepper plants of the invention can produce pungent (hot) or sweet (mild) fruits. In embodiments, the pepper plant is a sweet pepper plant (i.e., produces sweet pepper fruits), which typically produce immature green fruits that turn red, orange, yellow, red, purple or brown at maturity. The fruits can have any shape including, e.g., blocky or conical. In embodiments, the fruits are orange, triangular in shape and seedless at maturity. Generally, plants according to the present invention are domesticated (e.g., cultivated) and produce commercially acceptable fruits (e.g., with respect to size, shape, color, yield, and the like). Pepper cultivar Navelito can produce seedless fruits or fruits with fertile seeds, depending on whether a male-fertile pepper plant is provided as pollen donor. In the absence of a male-fertile pepper plant, Navelito produces seedless fruits. Those skilled in the art will appreciate that male fertility can be restored to pepper cultivar Navelito or progeny thereof in the presence of an appropriate restorer gene(s).

"Plant." As used herein, the term "plant" includes plant cells, plant protoplasts, plant cell tissue cultures from which plants can be regenerated, plant calli, plant clumps, and plant cells that are intact in plants or parts of plants, such as leaves, embryos, cotyledons, hypocotyl, roots, root tips, anthers, pistils, flowers, ovules, fruit, stems, rootstocks, scions, and the like.

"Plant material". The terms "plant material" and "material obtainable from a plant" are used interchangeably herein and refer to any plant material obtainable from a plant including without limitation, leaves, stems, roots, flowers or flower parts, fruits, egg cells, zygotes, cuttings, cell or tissue cultures, rootstocks, scions, or any other part or product of the plant.

"Plant part". As used herein, a "plant part" includes any part, organ, tissue or cell of a plant including without limitation an embryo, meristem, leaf, cotyledon, hypocotyl, root, root tip, anther, flower, flower bud, pistil, ovule, shoot, stem, stalk, petiole, pith, capsule, a scion, a rootstock and/or a fruit including callus and protoplasts derived from any of the foregoing.

"Seedless". The fruits of pepper cultivar Navelito are essentially completely seedless, in the absence of a male-fertile pollen donor. However, even when producing seed-less fruits, there can be occasional fruits with seeds due to cross-pollination by insects transferring pollen from a male-fertile pepper plant to Navelito.

"Quantitative Trait Loci". Quantitative Trait Loci (QTL) refers to genetic loci that control to some degree, numeri-cally representable traits that are usually continuously dis-tributed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environ-mental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A pepper plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single locus converted". A single locus converted or conversion plant refers to a plant that is developed by plant breeding techniques (e.g., backcrossing), genome editing techniques, genetic transformation techniques and/or muta-tion techniques (e.g., chemical or radiation induced) wherein essentially all of the desired morphological and physiologi-cal characteristics of a line are recovered in addition to the single locus introduced into the line via the plant breeding, genome editing, genetic transformation or mutation tech-niques.

"Substantially equivalent characteristic". A characteristic that, when compared, does not show a statistically signifi-cant difference (e.g., p=0.05) from the mean.

"Transgene". A nucleic acid of interest that can be intro-duced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in oper-able association with exogenous regulatory elements such as a promoter) than is found in the native state. The transgene can encode a polypeptide or a functional non-translated RNA (e.g., RNAi).

Botanical Description of the Novel Pepper Plant of the Invention. Pepper cultivar Navelito is cytoplasmic male sterile (CMS) and parthenocarpic, producing seedless fruits that are orange at maturity (in the absence of a male-fertile pepper plant as a pollen donor). The mature fruit is also mild, sweet, and triangular in shape. Navelito is a three-line hybrid ([P7M14×P7M13]×P7M11), where lines P7M14×P7M13 are isogenic that only differ in the sterility trait (line P7M14 is CMS, line P7M13 is the isogenic maintainer of line P7M14, and line P7M11 is the male). All three of these lines are proprietary and non-commercial. Because Navelito is male sterile and has a parthenocarpic trait, it can reliably produce seedless fruits by conventional cultivation methods, as long as fertilization by a male-fertile plant is avoided. In the presence of a male-fertile plant, pepper cultivar Navelito can be used in breeding as a female parent. Additional physiological and morphological characteristics of pepper cultivar Navelito are provided below in Table 1

TABLE 1

Characteristics of hybrid Navelito (as observed in plants grown in the greenhouse in 2018 Fall season in El Ejido, Spain).

| Descriptor | Navelito |
|---|---|
| Seedling: | |
| Seedling: anthocyanin coloration of the hypocotyl | Present |
| Plant: | |
| Plant: habit | Upright |
| Plant: length of stem | Short to medium |
| Plant: shortened internode (in upper part) | Absent |
| Plant: anthocyanin coloration of nodes | Present |
| Stem: | |
| Stem: intensity of anthocyanin coloration of nodes | Weak |
| Stem: hairiness of nodes | Very weak to weak |
| Stem: plant height | Medium |
| Leaf: | |
| Leaf: length of blade | Medium |
| Leaf: width of blade | Medium |
| Leaf: intensity of green color | Medium to dark |
| Leaf: shape | Ovate |
| Leaf: undulations of margin | Weak to medium |
| Leaf: blistering | Very weak |
| Leaf: profile in cross section | Moderately concave |
| Leaf: glossiness | Weak to medium |
| Peduncle: | |
| Peduncle: attitude | Semi-drooping |
| Flower: | |
| Flower: anthocyanin coloration of anther | Present |
| Fruit: | |
| Fruit: color (before maturity) | Green |
| Fruit: intensity of color (before maturity) | Medium to dark |
| Fruit: anthocyanin coloration | Absent |
| Fruit: attitude | Drooping |
| Fruit: length | Short |
| Fruit: diameter | Narrow |
| Fruit: ratio length/diameter | Large |
| Fruit: length (cm) | 7 |
| Fruit: diameter (cm) | 4 |
| Fruit: ratio numerical length/diameter | 1.75 |
| Fruit: shape in longitudinal section | Moderately triangular |
| Fruit: shape in cross section (at level of placenta) | Elliptic |
| Fruit: sinuation of pericarp at basal part | Very weak to weak |
| Fruit: sinuation of pericarp excluding basal part | Weak |
| Fruit: texture of surface | Smooth or very slightly wrinkled |
| Fruit: color (at maturity) | Orange |
| Fruit: intensity of color (at maturity) | Medium to dark |
| Fruit: glossiness | Medium |
| Fruit: stalk cavity | Absent |
| Fruit: shape of apex | Moderately acute |
| Fruit: Depth of interloculary grooves | Very shallow to shallow |
| Fruit: number of locules | Predominantly two |
| Fruit: thickness of flesh | Thin to medium |
| Fruit: capsaicin per gram dry fruit (mg) | 0 |
| Fruit: Scoville units (dry fruit) | 0 |
| Fruit: average fruit weight (g) | 20 |
| Stalk: | |
| Stalk: length | Short |
| Stalk: thickness | Thin |
| Calyx: | |
| Calyx: aspect | Non-enveloping |
| Placenta: | |
| Placenta: capsaicin in placenta | Absent |
| Timing: | |
| Timing: time of beginning of flowering (first flower on second flowering node) | Very early to early |
| Timing: time of maturity | Early |

TABLE 1-continued

Characteristics of hybrid Navelito (as observed in plants grown in the greenhouse in 2018 Fall season in El Ejido, Spain).

| Descriptor | Navelito |
|---|---|
| Disease resistances: | |
| Tobamovirus: Pathotype 0 (Tm: 0) | Resistant |
| Tomato Spotted Wilt Virus: Pathotype 0 (TSWV: 0) | Resistant |
| Leveillula taurica | Intermediate resistance |
| Group: | |
| Group: pepper type | Pimiento |

Tissue Culture.

In embodiments, pepper plants can be propagated by tissue culture and regeneration. Tissue culture of various tissues of pepper and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28 (2), 139-145 (1992). The state of the art is such that these methods of obtaining plants are routinely used and have a very high rate of success. Thus, another aspect of this invention is to provide cells which upon growth and differentiation produce pepper plants having desired characteristics of pepper cultivar Navelito. Optionally, pepper plants can be regenerated from the tissue culture of the invention comprising all the physiological and morphological characteristics of pepper cultivar Navelito.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Additional Breeding Methods.

This invention is also directed to methods for producing a pepper plant by crossing a first parent pepper plant with a second parent pepper plant wherein one of the parent pepper plants is a plant of pepper cultivar Navelito used as female. In embodiments, the second pepper plant used as a male comprises a parthenocarpic trait. In embodiments, the second pepper plant used as male does not comprise a parthenocarpic trait. In embodiments, the pepper plant used as a male comprises a restorer of CMS. In embodiments, the pepper plant used as a male does not comprise a restorer of CMS. Any of the following exemplary methods using pepper cultivar Navelito are part of this invention including without limitation double haploid technology, crosses to populations, and the like. All plants produced using pepper cultivar Navelito as a parent are within the scope of this invention, including those developed from pepper plants derived from pepper cultivar Navelito. Further, an exogenous transgene can be introduced into the pepper cultivar of the invention or a progenitor thereof (e.g., a parent line). The transgene can be introduced by traditional breeding methods or through transformation of the cultivar of the invention by any of a number of protocols known to those of skill in the art.

Those skilled in the art will appreciate that peppers can be readily crossed with other peppers, e.g., another *Capsicum* species including without limitation *C. annuum, C. baccatum, C. chinense, C. frutescens* or *C. pubescens*. In embodiments, the peppers of the invention are crossed with another *C. annuum*. Thus, the methods of the invention encompass crosses between pepper cultivar Navelito, and progeny and derivatives thereof, with other peppers including *C. annuum* or any other pepper type. Further, the peppers of the invention can be crossed with other sweet or hot peppers, and with peppers having any fruit shape (e.g., blocky or conical).

The following describes exemplary breeding methods that may be used with pepper cultivar Navelito in the development of further pepper plants. One such embodiment is a method for developing pepper cultivar Navelito progeny pepper plants in a pepper plant breeding program comprising: obtaining a plant, or a part thereof, of pepper cultivar Navelito, utilizing said plant or plant part as a source of breeding material, and selecting a pepper cultivar Navelito progeny plant with molecular markers in common with pepper cultivar Navelito and/or with morphological and/or physiological characteristics of pepper cultivar Navelito described herein. In representative embodiments, the progeny plant has at least 2, 3, 4, 5, 6, 7, 8. 9, 10 or more of the morphological and physiological characteristics of pepper cultivar Navelito (e.g., as described in Table 1), or even of all the morphological and physiological characteristics of pepper cultivar Navelito, so that said progeny pepper plant is not significantly different for said traits than pepper cultivar Navelito, as determined at the 5% significance level when grown in the same environmental conditions; optionally, with the presence of one or more desired additional traits (e.g., male fertility, disease resistance, pest or insect resistance, herbicide resistance, and the like). Breeding steps that may be used in the breeding program include pedigree breeding, backcrossing, mutation breeding, and recurrent selection. In conjunction with these steps, techniques such as RFLP-enhanced selection, genetic marker enhanced selection (for example, SNP or SSR markers), and the making of double haploids may be utilized.

Another representative method involves producing a population of pepper cultivar Navelito progeny pepper plants, comprising crossing pepper cultivar Navelito as female with another pepper plant as male (optionally, by hand pollination), thereby producing a population of pepper plants, which, on average, derive 50% of their alleles from pepper cultivar Navelito. A plant of this population may be selected and repeatedly selfed or sibbed with a pepper plant resulting from these successive filial generations. Another approach is to make double haploid plants to achieve homozygosity. One embodiment of this invention is a pepper plant produced by these methods and that has obtained at least 50% of its alleles from pepper cultivar Navelito. In embodiments, the methods of the invention produce a population of pepper plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from pepper cultivar Navelito, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pepper cultivar Navelito. One representative embodiment of this invention is the pepper plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from pepper cultivar Navelito, and optionally may be the result of a breeding process comprising one or two breeding crosses and one or more of selfing, sibbing, backcrossing and/or double haploid techniques in any combination. In embodiments, the breeding process does not include a breeding cross, and comprises double haploid technology.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). In embodiments, the invention encompasses progeny plants having a combination of at least 2, 3, 4, 5 or 6 characteristics as described herein for pepper cultivar Navelito, so that said progeny pepper plant is not significantly different for said traits than pepper cultivar Navelito, as determined at the 5% significance level when grown in the same environmental conditions. Using techniques described herein and those known in the art, molecular markers may be used to identify said progeny plant as progeny of pepper cultivar Navelito. Mean trait values may be used to determine whether trait differences are significant, and optionally the traits are measured on plants grown under the same environmental conditions.

Progeny of pepper cultivar Navelito may also be characterized through their filial relationship with pepper cultivar Navelito, as for example, being within a certain number of breeding crosses of pepper cultivar Navelito. A breeding cross is a cross made to introduce new genetics into the progeny, and is distinguished from a cross, such as a self or a sib cross, made to select among existing genetic alleles. The lower the number of breeding crosses in the pedigree, the closer the relationship between pepper cultivar Navelito and its progeny. For example, progeny produced by the methods described herein may be within 1, 2, 3, 4, 5 or more breeding crosses of pepper cultivar Navelito.

In representative embodiments, a plant derived from pepper cultivar Navelito is a double haploid plant or an inbred plant.

In embodiments, a derived plant from pepper cultivar Navelito comprises a desired added trait. In representative embodiments, a pepper plant derived from pepper cultivar Navelito comprises all of the morphological and physiological characteristics of pepper cultivar Navelito (e.g., as described herein, in particular, in Table 1). In embodiments, the pepper plant derived from pepper cultivar Navelito comprises all or essentially all of the morphological and physiological characteristics of pepper cultivar Navelito (e.g., as described herein, in particular, in Table 1), with the addition of a desired added trait. In embodiments, a pepper plant derived from pepper cultivar Navelito is characterized by comprising both CMS and a parthenocarpic trait resulting in the production of seedless fruits (in the absence of a male fertile parent) that optionally are orange at maturity, and as a further option are triangular in shape. The pepper plant may optionally further be characterized by comprising one or more of the disease resistances of pepper cultivar Navelito (e.g., as shown in Table 1).

Genetic Transformation.

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species, the same species or an artificial sequence, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of pepper plants disclosed herein.

Genetic engineering techniques can be used (alone or in combination with breeding methods) to introduce one or more desired added traits into plant, for example, pepper cultivar Navelito or a progenitor (e.g., a parent line), progeny or pepper plant derived therefrom. Once a transgene has been introduction into a plant by genetic transformation, it can be transferred to other plants via conventional breeding.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid and can be used alone or in combination with other plasmids, to provide transformed pepper plants using transformation methods as described herein to incorporate transgenes into the genetic material of the pepper plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase, selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Many suitable promoters are known in the art and can be selected and used to achieve the desired outcome.

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

US 12,599,100 B2

17

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981).

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to confer resistance to plant pests (e.g., nematode or insect) or disease (e.g., fungal, bacterial or viral), transgenes that confer herbicide tolerance, transgenes that confer male fertility, and transgenes that confer or contribute to a value-added trait such as increased nutrient content (e.g., iron, nitrate), increased sweetness (e.g., by introducing a transgene coding for monellin), modified fatty acid metabolism (for example, by introducing into a plant an antisense sequence directed against stearyl-ACP desaturase to increase stearic acid content of the plant), modified carbohydrate composition (e.g., by introducing into plants a transgene coding for an enzyme that alters the branching pattern of starch), modified fruit color (e.g., external fruit color), or modified flavor profile of the fruit.

In embodiments, the transgene encodes a non-translated RNA (e.g., RNAi) that is expressed to produce targeted inhibition of gene expression, thereby conferring the desired trait on the plant.

In embodiments, the transgene encodes the machinery used for genome editing techniques.

Any transgene, including those exemplified above, can be introduced into the pepper plants of the invention through a variety of means including, but not limited to, transformation (e.g., genetic engineering techniques), conventional breeding, and introgression methods to introduce the transgene into other genetic backgrounds.

Methods for Plant Transformation.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993). Commonly used plant transformation methods include Agrobacterium-mediated transformation and direct transgene transfer methods (e.g., microprojectile-mediated transformation, sonication, liposome or spheroplast fusion, and electroporation of protoplasts or whole cells).

Following transformation of plant target tissues, expression of selectable marker transgenes (e.g., as described above) allows for preferential selection of transformed cells, tissues and/or plants, using regeneration and selection methods now well known in the art.

The foregoing methods for transformation are typically used to produce a transgenic pepper line. The transgenic pepper line can then be crossed with another (non-transgenic or transgenic) line in order to produce a new transgenic pepper line. Alternatively, a transgene that has been engineered into a particular plant using transformation techniques can be introduced into another plant or line using traditional breeding (e.g., backcrossing into a parental line) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene.

Locus Conversion.

The term "locus converted plant" or plant having a "locus conversion" (and similar terms) as used herein refers to those plants that are developed, for example, by backcrossing, genome editing, genetic transformation and/or mutation (e.g., into a parental line), wherein essentially all of the desired morphological and physiological characteristics of a variety are recovered in addition to the one or more genes introduced into the variety. To illustrate, in particular embodiments, backcrossing into a parental line can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene/locus for the desired characteristic is termed the "nonrecurrent" or "donor parent." This terminology refers to the fact that the nonrecurrent parent is generally used one time in the breeding e.g., backcross) protocol and therefore does not recur. The gene/locus that is transferred can be a native gene/locus, a mutated native gene/locus or a transgene introduced by genetic engineering techniques into the plant (or ancestor thereof). The parental plant into which the locus/loci from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the locus/loci of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred locus/loci and associated trait(s) from the nonrecurrent parent.

Genetic Analysis of Pepper Cultivar Navelito.

The invention further provides a method of determining a genetic characteristic of pepper cultivar Navelito or a progeny thereof, e.g., a method of determining a genotype of pepper cultivar Navelito or a progeny thereof. In embodiments, the method comprises detecting in the genome of a Navelito plant, or a progeny plant thereof, at least a first polymorphism, e.g., by detecting a nucleic acid marker by a method comprising nucleic acid amplification and/or nucleic acid sequencing. To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

DEPOSIT

Applicants have made a deposit of at least 625 seeds of pepper cultivar Navelito with the Provasoli-Guillard National Center for Marine Algae and Microbiota (NCMA) at Bigelow Laboratory for Ocean Sciences, 60 Bigelow Drive, East Boothbay, Me., 04544 U.S.A. under NCMA Accession No. 202403002 on Mar. 1, 2024. This deposit will be maintained in the NCMA depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. During the pendency of this application, access to the deposited material will be afforded to the Commissioner on request. All restrictions on the availability of the deposited material from the NCMA to the public will be irrevocably removed upon granting of the patent. Applicants impose no restrictions on the availability of the deposited material from the NCMA; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application directed to a variety, all restrictions on the availability to the public of that variety will be irrevocably removed by affording access to the deposit of at least 625 seeds of the same variety with the NCMA.

The foregoing invention has been described in detail by way of illustration and example for purposes of clarity and understanding. However, it will be apparent that certain changes and modifications such as single locus modifications and mutations, somaclonal variants, variant individuals selected from large populations of the plants of the instant inbred and the like may be practiced within the scope of the invention. Thus, although the foregoing invention has been described in some detail in this document, it will be obvious that changes and modifications may be practiced within the scope of the invention.

What is claimed is:

1. A seed that produces pepper cultivar Navelito, a representative sample of seed having been deposited under NCMA Accession No. 202403002.

2. A plant of pepper cultivar Navelito grown from the seed of claim 1.

3. A pepper plant having all the physiological and morphological characteristics of the pepper plant of claim 2.

4. A seed that produces the plant of claim 3.

5. A plant part of the pepper plant of claim 2.

6. The plant part of claim 5, wherein the plant part is a fruit, a scion, a rootstock, a shoot, an anther, an ovule, a root, a leaf, or a cell.

7. A tissue culture of regenerable cells of the plant of claim 2.

8. A pepper plant regenerated from a tissue culture of regenerable cells of the plant of claim 2, wherein the regenerated pepper plant comprises all of the physiological and morphological characteristics of the plant of claim 2.

9. A method of producing pepper seed, the method comprising crossing the plant of claim 2 as female with a second pepper plant as male and harvesting the resulting seed.

10. The method of claim 9, wherein the crossing is done by hand pollination.

11. A method of developing a pepper line in a pepper plant breeding program using plant breeding techniques, which include employing a pepper plant, or its parts, as a source of plant breeding material, the method comprising:
    (a) obtaining the pepper plant, or parts thereof, of claim 2 as a source of breeding material; and
    (b) applying plant breeding techniques.

12. A method for producing a seed of a pepper plant derived from the plant of claim 2, the method comprising:
    (a) crossing a pepper plant of pepper cultivar Navelito as female with a second pepper plant as male;
    (b) allowing seed to form;
    (c) growing a plant from the seed of step (b) to produce a plant derived from pepper cultivar Navelito;
    (d) selfing the plant of step (c) or crossing it to a second pepper plant to form additional pepper seed derived from pepper cultivar Navelito; and
    (e) optionally repeating steps (c) and (d) one or more times to generate further derived pepper seed from pepper cultivar Navelito, wherein in step (c) a plant is grown from the additional pepper seed of step (d) in place of growing a plant from the seed of step (b).

13. The method of claim 12, wherein the crossing in step (a) is done by hand pollination.

14. A method of producing a seedless pepper fruit, the method comprising:
    (a) growing the plant of claim 2 to produce a pepper fruit; and
    (b) harvesting the pepper fruit from the plant.

15. A method of vegetatively propagating the plant of claim 2, the method comprising:
    (a) collecting tissue capable of being propagated from a plant of pepper cultivar Navelito;
    (b) cultivating the tissue to obtain proliferated shoots; and
    (c) rooting the proliferated shoots to obtain rooted plantlets.

16. The method of claim 15, further comprising growing plants from the rooted plantlets.

17. A plant obtained by the method of claim 16, wherein the plant comprises all of the physiological and morphological characteristics of pepper cultivar Navelito.

18. A method of producing a plant of pepper cultivar Navelito comprising a desired added trait, the method comprising introducing a transgene conferring the desired trait into the plant of claim 2.

19. A pepper plant produced by the method of claim 18, wherein the pepper plant is a transformed pepper plant comprising the desired added trait and otherwise all of the physiological and morphological characteristics of pepper cultivar Navelito.

20. A seed that produces the plant of claim 19, wherein the seed produces a transformed plant of pepper cultivar Navelito that has the desired added trait.

21. A method of determining a genotype of pepper cultivar Navelito, the method comprising:

(a) obtaining a sample of nucleic acids from the plant of claim 2; and (b) detecting a polymorphism in the nucleic acid sample using molecular biology techniques.

* * * * *

22